United States Patent [19]
Neese et al.

[11] Patent Number: 6,086,549
[45] Date of Patent: Jul. 11, 2000

[54] APPARATUS AND METHOD FOR TREATING FEMALE URINARY INCONTINENCE

[75] Inventors: Jon Neese; Ben D. Shirley, both of Salt Lake City, Utah

[73] Assignee: Utah Medical Products, Inc., Midvale, Utah

[21] Appl. No.: 08/887,882

[22] Filed: Jul. 3, 1997

[51] Int. Cl.$^7$ ..................................................... A61B 5/103
[52] U.S. Cl. ........................... 600/587; 600/554; 607/41; 607/138
[58] Field of Search ..................................... 600/546, 554, 600/587, 591; 607/41, 138, 36, 116

[56] References Cited

U.S. PATENT DOCUMENTS

| | | |
|---|---|---|
| 3,669,100 | 6/1972 | Csanad ....................................... 128/32 |
| 3,933,147 | 1/1976 | Du Vall et al. ........................... 600/591 |
| 4,311,140 | 1/1982 | Bridgman ................................. 128/276 |
| 4,515,167 | 5/1985 | Hochman ................................. 600/591 |
| 4,873,990 | 10/1989 | Holmes et al. .......................... 600/591 |
| 4,881,526 | 11/1989 | Johnson et al. .......................... 128/788 |
| 4,909,263 | 3/1990 | Norris ...................................... 600/591 |
| 5,010,895 | 4/1991 | Maurer et al. ........................... 600/591 |
| 5,184,619 | 2/1993 | Austin ..................................... 600/591 |
| 5,314,465 | 5/1994 | Maurer et al. ........................... 607/138 |
| 5,370,671 | 12/1994 | Maurer et al. ........................... 607/138 |
| 5,385,577 | 1/1995 | Maurer et al. ............................. 607/41 |
| 5,483,832 | 1/1996 | Pauser et al. ............................. 600/591 |
| 5,562,717 | 10/1996 | Tippey et al. .............................. 607/41 |
| 5,571,118 | 11/1996 | Boutos .................................... 607/138 |
| 5,573,499 | 11/1996 | McAllister ................................. 601/70 |
| 5,649,976 | 7/1997 | Malewicz ................................ 607/138 |
| 5,800,501 | 9/1998 | Sherlock ................................. 607/138 |
| 5,881,731 | 3/1999 | Remes .................................... 128/885 |

OTHER PUBLICATIONS

INNOVA, "INNOVA Feminine Incontinence Treatment System Design Rationale", Empi Catalog, 1992.

"Maximal Electrostimulation of the Pelvic Floor in Female Idiopathic Detrusor Instability and Urge Incontinence", B.C. Eriksen, S. Bergman, S.H. Eik–Nes, *Neurology and Urodynamics*, 1989.

"A Comparative Study of Pelvic Floor Training and Electrical Stimulation for the Treatment of Genuine Female Stress Urinary Incontinence", Inger Hahn, Solveig Sommar, Magnus Fall, *Neurology and Urodynamics*, 1991.

"The Role of Biofeedback in Kegel Exercise Training for Stress Urinary Incontinence", Kathryn Larsen Burgio Ph.D., J. Courtland Robinson, M.D., Bernard T. Engel, Ph.D., Gerontology Research Center, Oct. 1985.

"Progressive Resistance Exercise in the Functional Restoration of the Perineal Muscles", Arnold H. Kegel, M.D., F.A.C.S., Los Angeles, California, Aug. 1948.

"Diagnosis and Management of Female Urinary Incontinence in General Practice", Jacqueline v. Jolleys, *Journal of the Royal College of General Practitioners*, Jul. 1989.

(List continued on next page.)

*Primary Examiner*—Max Hindenburg
*Assistant Examiner*—Charles Marmor, II
*Attorney, Agent, or Firm*—Clayton, Howarth & Cannon, P.C.

[57] ABSTRACT

The present invention provides an efficient and cost effective device for applying electrical stimulation to a body cavity. Preferred embodiments of the invention also provide the function of measuring the pressure exerted by the body cavity. The present invention is particularly useful when treating urinary incontinence in females. By providing electrical stimulation to the vagina, the present invention strengthens the pelvic floor muscles to improve urinary continence. The preferred embodiments of the invention which provide the function of measuring the pressure exerted by the body cavity convey to a user in a humanly perceptible manner the pressure exerted by the body cavity in order to provide feedback on the strengthening of the pelvic floor muscles. Most advantageously, a carrier structure which is inserted into the body cavity is fabricated from a low cost material, such as an injection molded thermoplastic material. The electrodes placed on the carrier structure can be fabricated separately from, and from a material different than, that used to fabricate the carrier structure. The pressure transducer preferably includes a semiconductor diaphragm sensitive to changes in pressure.

31 Claims, 4 Drawing Sheets

OTHER PUBLICATIONS

"Long–Term Electrostimulation of the Pelvic Floor: Primary Therapy in Female Stress Incontinence?", B.C. Eriksen, S.H. Eik–Nes, Jan. 6, 1988.

"Controlled Trial of Pelvic Floor Exercises in the Treatment of Urinary Stress Incontinence in General Practice", Toine L.M. Largo–Janssen, Frans M.J. DeBruyne, Anton J.A. Smits, Chris Van Weel, *British Journal of General Practice*, Nov. 1991.

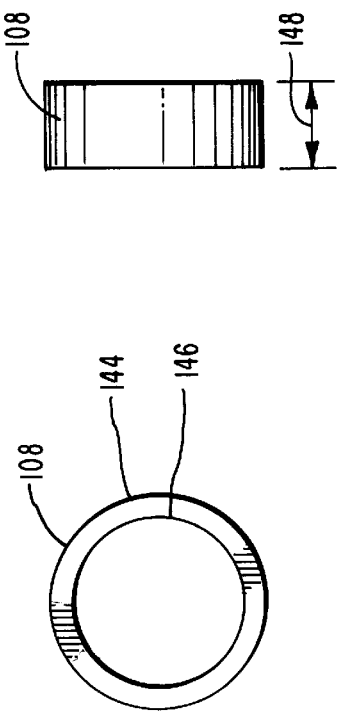
FIG. 6A
FIG. 6B
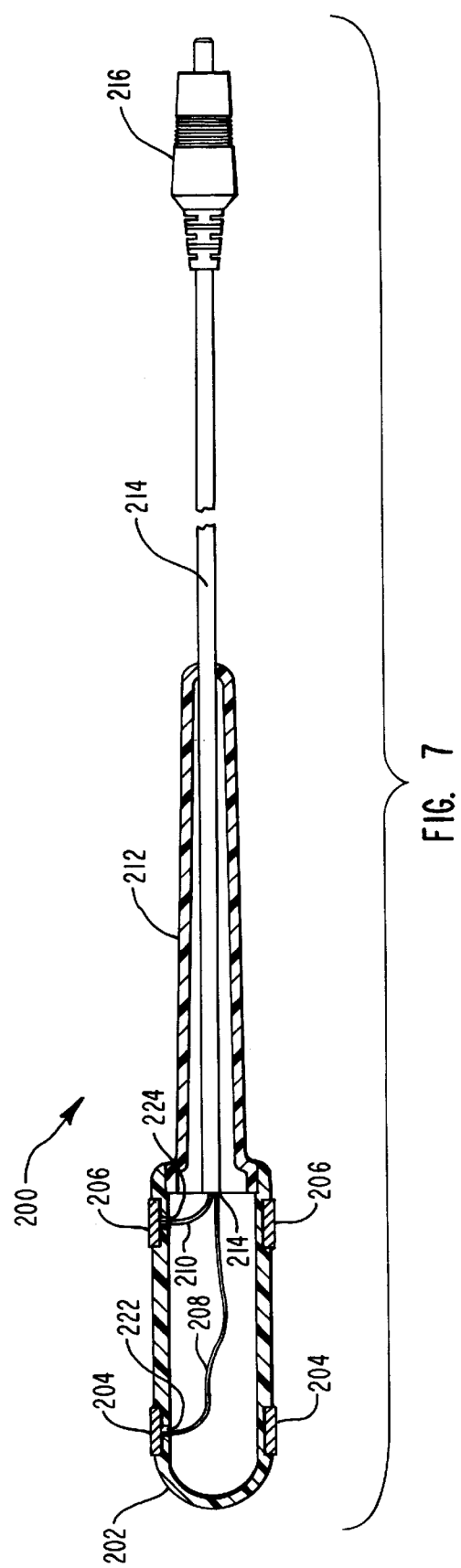
FIG. 7

APPARATUS AND METHOD FOR TREATING FEMALE URINARY INCONTINENCE

BACKGROUND

1. The Field of the Invention

This invention relates to methods and apparatus used to treat incontinence. More particularly, the present invention is related to methods and apparatus for treating urinary incontinence in females.

2. The Prior Art

Urinary incontinence is a problem which afflicts numerous people in many parts of the world, particularly women and the aged. Urinary incontinence currently plagues 10–35 percent of adults and at least half of the nursing home residents in the United States. More specifically, in the United States, among the population between 15 and 64 years of age, the prevalence of urinary incontinence in men ranges from 1.5 to 5 percent and in women from 10 to 30 percent. For noninstitutionalized persons older than 60 years of age, the prevalence of urinary incontinence ranges from 15 to 35 percent, with women having twice the prevalence of men. Between 25 and 30 percent of those identified as incontinent have frequent incontinence episodes, usually daily or weekly.

Those familiar with the condition will appreciate that urinary incontinence is very prevalent among adult women, mostly in the form of stress incontinence, with many patients benefitting from some kind of treatment. Because of the social stigma of urinary incontinence, many sufferers do not even report the problem to a health care provider. As a result, this medical problem is vastly under diagnosed and under reported.

For individuals which are otherwise capable of caring for themselves, incontinence is particularly embarrassing, causes distress, loss of sleep, and inconvenience for the afflicted individual. Afflicted individuals must also spend money for absorbent pads, diapers, rubber sheeting and for cleaning of soiled clothing.

There are two types of urinary incontinence which are generally recognized: urge incontinence and stress incontinence. The symptom of urge incontinence is the involuntary loss of urine associated with a strong desire to void (urgency). Although urge incontinence can be associated with neurologic disorders, it also occurs in individuals who appear to be neurologically normal.

Stress urinary incontinence is the involuntary loss of urine during coughing, sneezing, laughing, or other physical activities that increase intra-abdominal pressure. The most common cause of stress urinary incontinence in women is urethral hypermobility, or significant displacement of the urethra and bladder neck during exertion when intra-abdominal pressure is raised. Stress urinary incontinence may also be caused by an intrinsic urethral sphincter deficiency, which may be due to congenital sphincter weakness in patients with myelomeningocele, epispadias, or pelvic denervation, or may be acquired after prostatectomy, trauma, radiation therapy, or a sacral cord lesion. In stress urinary incontinence, the urethral sphincter is unable to generate enough resistance to retain urine in the bladder, especially during stress maneuvers. Patients with stress urinary incontinence often leak continuously or with minimal exertion.

When both symptoms are present, the incontinence is called mixed urinary incontinence. Mixed urinary incontinence is common in women, especially older women. Often, however, one symptom (urge or stress) is often more bothersome to the patient than the other. Identifying the most bothersome symptom is important in targeting diagnostic and therapeutic interventions.

Treatments for incontinence include surgery, drug therapy, physical exercises, and electrical stimulation. In the late 1940s, Arnold Kegel described pelvic floor exercises as a treatment option in urinary incontinence. The purpose of the exercises, now often referred to as "Kegal exercises," is to increase the muscle volume and to develop stronger reflex contractions following a quick rise in intra-abdominal pressure. Lack of awareness of these muscles is common in women, and Kegel stressed the importance of learning how to perform the exercises correctly. In controlled studies on the effect of pelvic floor exercises, it has been shown that such exercises resulted in improved urinary continence in women. Jolleys, J. V., "Diagnosis and Management of Female Urinary Incontinence in General Practice" *J. R. Coll. Gen. Pract.* 1989; 39: 277–9; Lagro-Janssen, T. L. M., Debruyne, F. M., Smits, A. J., Van Weel, C., "Controlled Trial of Pelvic Floor Exercises in the Treatment of Urinary Stress Incontinence in General Practice" *Br. J. Gen. Pract.* 1991; 41: 445–9. Kegal exercises strengthen the pelvic floor muscles and in many individuals result in improved continence. Importantly, it is preferred that the treatment for incontinence be the least invasive treatment possible and that it be safe, effective, and relatively inexpensive.

To help women gain control over their pelvic floor muscles several devices have been proposed. Kegel developed the perineometer, a pneumatic vaginal rubber tube for recording intravaginal pressure. Kegel, A. H., "Progressive Resistance Exercise in the Functional Restoration of the Perineal Muscles" *Am. J. Obstet. Gyncol.* 1948; 56: 238–49. It has also been shown that visual feedback of bladder pressure, abdominal pressure, and sphincter activity is more effective than simple verbal performance feedback. Burgio, K. L., "The Role of Biofeedback in Kegel Exercise Training for Stress Urinary Incontinence" *Am. J. Obstet. Gynecol.* 1986; 154: 58–64. Such devices are too sophisticated, however, for routine use in general practice, and particularly for unsupervised use by a patient.

In an effort to provide a treatment which can be carried out by an unsupervised patient, vaginal cones have been proposed as an aid to pelvic floor muscle training. Typically, one of the cones is inserted and carried in the vagina for 15 minutes twice a day. The vaginal cones provide sensory feedback which makes the pelvic floor contract around the cone and retain it. As the pelvic floor muscles are strengthened, the weight of the cones is gradually increased. It has been shown that vaginal cones have been at least as effective as routine pelvic floor muscle exercises (Kegel exercises) and require less time to teach.

While Kegel exercises and exercises using vaginal cones in many cases provides improved continence for many women, electrical stimulation of the pertinent muscles provides results in many individuals which are as good as, or better than, the other treatments and is still minimally invasive.

The use of transcutaneous electrical stimulation in a body cavity has been available for some time now and is recognized as being safe and effective. Transcutaneous intravaginal electrical stimulation is particularly recognized as being safe and effective for many women suffering from urinary incontinence. Electrical stimulation of the various branches of the pudendal nerve which lead to the muscles of the pelvic floor have been found to cause contraction of these muscles acutely and strengthening of the muscles via stimulation. With adequate electrical stimulation treatment in this manner, the patient may be completely cured of incontinence and may no longer require further assistance or treatment to remain continent.

Transcutaneous electrical stimulation can be used to treat both stress incontinence and urge incontinence. In transcutaneous electrical stimulation, an electrical signal is applied to electrodes inserted into the vagina. The electrical signal is usually in the form of a plurality of pulses. The electrical pulses are transferred by the electrodes to the vaginal wall adjacent to the desired muscles causing contraction of the muscles of the pelvic floor. As a result thereof, the external sphincter of the urethra is constricted, preventing the undesired outward flow of urine. Generally, urge incontinence is treated by short-term maximal stimulation while stress incontinence is usually treated by long-term stimulation of a lower intensity. Eriksen, B. C., Eik-Nes, S., "Long-term Electrostimulation of the Pelvic Floor: Primary Therapy in Female Stress Incontinence?" *Urol. Int.* 1989; 44: 90–5; Hahn, I., Sommer, S., Fall, M., "A comparative study of pelvic floor training and electrical stimulation for the treatment of genuine female stress urinary incontinence" *Neurourol. Urodyn.* 1991; 10: 545–54; Eriksen, B. C., "Maximal Electrostimulation of the Pelvic Floor in Female Idiopathic Detrusor Instability and Urge Incontinence" *Neurourol. Urodyn.* 1989; 8: 219–30.

Significantly, it many be necessary to continue electrostimulation treatments of the pelvic floor muscles for many months to obtain the desired result. Thus, it is very desirable that the patient be able to carry out the electrical stimulation treatment without the immediate supervision of a medical practitioner, preferably in the patient's home. Thus, there is a need to provide a system which allows an individual to treat themselves without the immediate supervision of a health care practitioner.

BRIEF SUMMARY AND OBJECTS OF THE INVENTION

In view of the above described state of the art, the present invention seeks to realize the following objects and advantages.

It is a primary object of the present invention to provide a system for treating female urinary incontinence.

It is also an object of the present invention to provide a system for treating female urinary incontinence which can be used by a patient without the immediate supervision of a medical practitioner.

It is a further object of the present invention to provide a device for providing vaginal electrical stimulation which is inexpensive.

It is another object of the present invention to provide a device for providing vaginal electrical stimulation which can be economically manufactured.

These and other objects and advantages of the invention will become more fully apparent from the description and claims which follow, or may be learned by the practice of the invention.

The present invention provides an efficient and cost effective device for applying electrical stimulation to a body cavity. Preferred embodiments of the invention also provide the function of measuring the pressure exerted by the body cavity. The present invention is particularly useful when treating urinary incontinence in females. By providing electrical stimulation to the vagina, the present invention strengthens the pelvic floor muscles to improve urinary continence. The preferred embodiments of the invention which provide the function of measuring the pressure exerted by the body cavity convey to a user in a humanly perceptible manner the pressure exerted by the body cavity in order to provide feedback on the strengthening of the pelvic floor muscles.

Preferred embodiments of the invention include a first conductive means for conveying an electrical current to the body cavity and a second conductive means, cooperating with the first conductive means, also for conveying an electrical current to the body cavity. The first conductive means and the second conductive means are preferably any structures now known in the art, or which become available in art, which can convey electrical current to a body part, and particularly includes electrodes consisting of carbon impregnated silicon rubber, silver, silver chloride, aluminum, chromium, or nickel all of which can be formed into a band shape.

The pressure sensing means provides the function of sensing the pressure exerted by the body cavity. In preferred embodiments of the present invention, the pressure sensing means includes a pressure transducer means for outputting an electrical pressure signal proportional to the pressure exerted thereon. The pressure transducer means is disposed in the body cavity during use. A means for conveying the electrical pressure signal to a location outside of the body cavity and a means for electrically isolating the pressure transducer means from the body cavity and for communicating the pressure from the body cavity to the pressure transducer means is also provided. The pressure transducer means can be any of a number of transducers now available or which become available in the future, a semiconductor diaphragm type of pressure transducer being presently preferred, such a thin-film strain gauge.

A means for supporting at least a portion of the first conductive means and at least a portion of the second conductive means in a spaced apart relationship within the body cavity is provided. Most advantageously, the means for supporting can be formed as a carrier structure which is fabricated from a low cost material, such as an injection molded thermoplastic material. The electrodes can be fabricated separately from, and from a material different than, that used to fabricate the carrier structure. Fabricating the electrodes and the carrier structure separately and from different materials provides advantages not otherwise available in the art. In some preferred embodiments of the invention, the electrodes are held in channels formed in the carrier structure.

The means for supporting also preferably holds at least a portion of the pressure sensing means within the body cavity such that the pressure exerted by the body cavity can be expressed as an electrical signal output from the pressure sensing means. The means for supporting holds the pressure sensor means in the proper position within the body cavity so that the pressure exerted within the body cavity is determined.

The pressure sensing means preferably comprises a pressure transducer which includes a semiconductor diaphragm sensitive to changes in pressure. The electrical signal generated by the pressure transducer is conveyed to a device which can express the pressure in a humanly perceptible manner, preferably via a visual display. The pressure sensing means further preferably comprises a means for electrically isolating the pressure transducer from the surrounding body cavity and also for communicating the pressure from the body cavity to the pressure transducer means. These functions are preferably performed by structures comprising a channel formed in the means for supporting, the pressure transducer being disposed in the channel. A flexible band is placed in the channel and over the pressure transducer such that as the body cavity exerts pressure on the flexible band the flexible band flexes in response thereto. Also, a gelatinous medium is preferably disposed between the flexible band and the pressure transducer such that the pressure created by the flexing of the flexible band is transmitted to the pressure transducer.

A means for generating a stimulation current and conveying the stimulation current to the first and second conductive bands is preferably provided at a location outside of the body cavity. The means for generating and conveying preferably comprise electrical conductors and a plug, as known in the industry.

Preferred embodiments of the present invention also include means for venting fluid from within the body cavity to a location outside the body cavity. The means for venting preferably comprises a vent orifice provided on one end of the means for supporting and a vent tube connecting the vent orifice to a location outside of the body cavity. A handle is also preferably provided on some embodiments of the present invention, the handle extending from the means for supporting.

One preferred most economical embodiment of the present invention includes a means for generating an electrical stimulation signal and a device configured for insertion into and retention in the body cavity, the device consisting essentially of first and second conductive means for conveying an electrical current to the body cavity, means for supporting the first and second conductive means in the body cavity fabricated from an injection molded thermoplastic material, and means for conveying an electrical stimulation signal from a location outside of the body cavity to the first and second conductive means such that electrical stimulation is applied to the body cavity.

BRIEF DESCRIPTION OF THE DRAWINGS

In order to better appreciate how the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIGS. 6A and 6B are detailed views of a preferred electrode for use with the embodiment of FIG. 1.

FIG. 7 is a cross sectional view of another embodiment of the present invention.

DETAILED DESCRIPTION OF THE PREFERRED EMBODIMENTS

Reference will now be made to the drawings wherein like structures will be provided with like reference designations.

Figure 1:
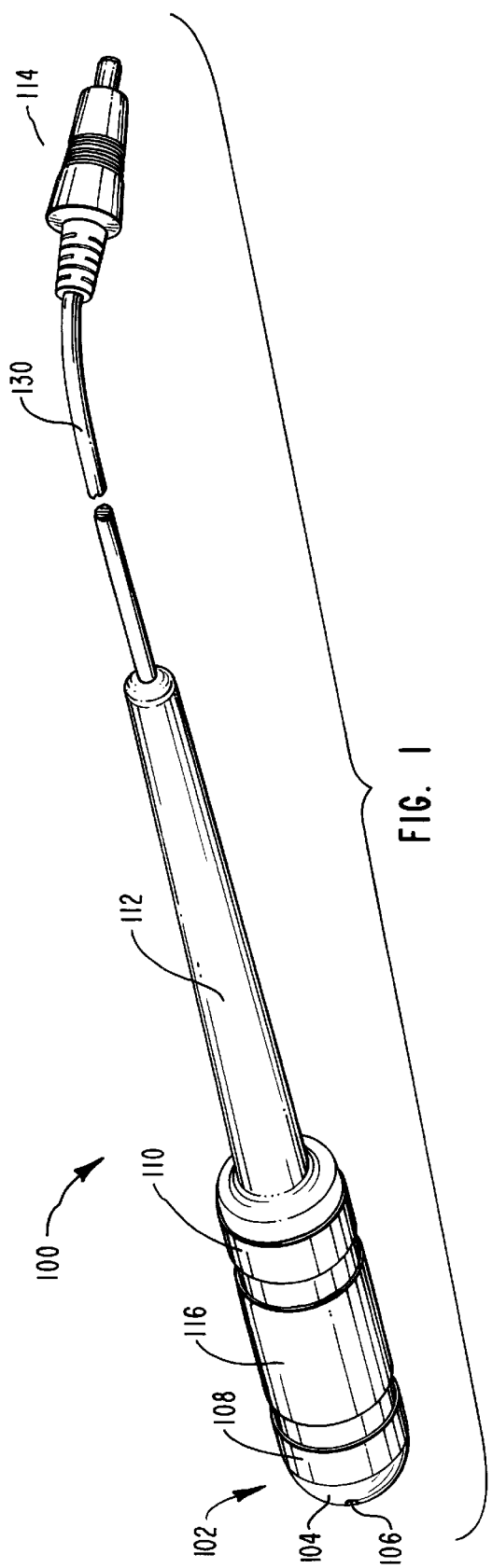
FIG. 1 is a perspective view of a presently preferred embodiment of the present invention.

FIG. 1 provides a perspective view of a probe assembly 100 in accordance with the present invention As will be understood from an examination of this disclosure, the present invention provides a system and method which allows a user to administer electrical stimulation to pelvic floor muscles without the immediate supervision of a medical practitioner. As explained earlier, electrical stimulation of the pelvic floor muscles is an effective and safe treatment for female urinary incontinence.

Figure 2:
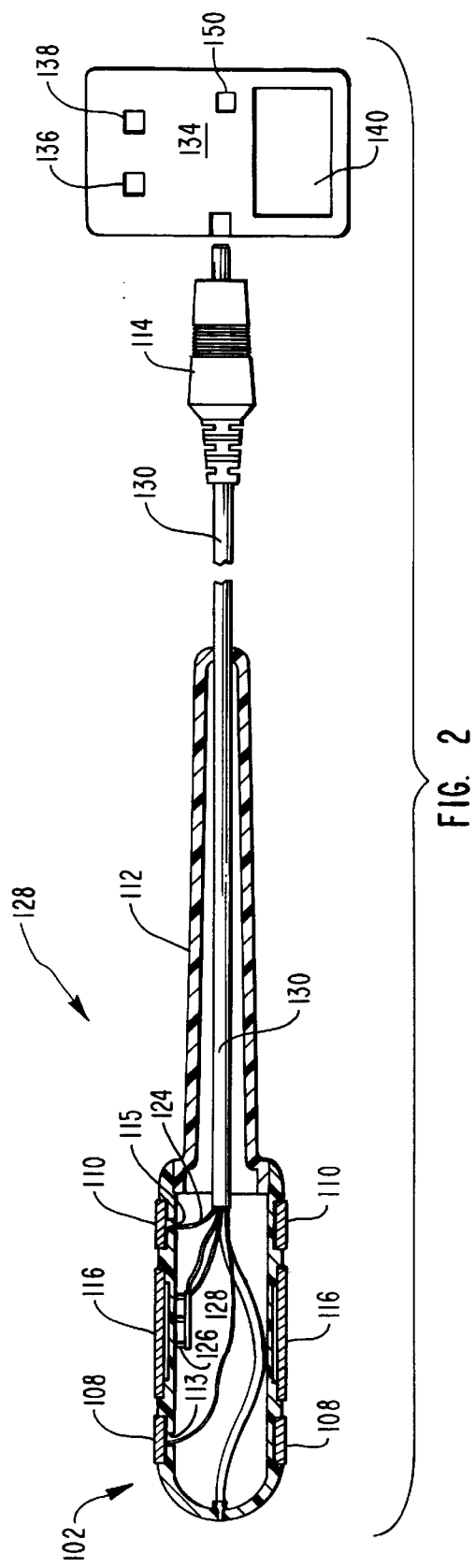
FIG. 2 is a is a cross sectional view of the apparatus represented in FIG. 1.

FIG. 2 provides a cross sectional view of the probe assembly 100 represented in FIG. 1. In order to provide the clearest description of the represented preferred embodiment of the present invention, reference will be made to FIG. 1 or FIG. 2, or to both figures simultaneously.

The probe assembly 100 includes an electrode assembly, generally designated at 102, and a handle 112. As seen best in the cross sectional view of FIG. 2, an electrode shell 104 is hollow. Both the electrode shell 104 and the handle 112 are preferably fabricated using injection molding techniques and a material such as medical grade polyvinyl chloride or another thermoplastic material.

Those skilled in the industry will appreciate that using polyvinyl chloride, or a similar thermoplastic material, to fabricate the electrode shell 104 and the handle 112, the probe 100 can be economically fabricated. In contrast, conventional teachings in the industry require that the pertinent structures be fabricated from an expensive medical grade silicone, a relatively difficult material to work with.

The preferred use of the probe 100 is for treatment of urinary incontinence in females. Thus, the electrode shell 104 is constructed to provide easy insertion and retention into a vagina. It is within the scope of the present invention to fabricate the electrode shell 104 in different sizes and shapes to provide for a close fit with a vaginal wall. It is also within the scope of the present invention to provide only one size and shape of electrode shell 104 for all users and still provide advantageous results. As will be understood further from an examination of this disclosure, it is further within the scope of the present invention to provide other structures for ensuring proper placement of the electrode shell 104 in a vagina and/or for ensuring that electrical stimulation is conveyed to a vaginal wall and the pelvic floor muscles.

Provided on the exterior of the electrode shell 104 are a first electrode 108 and a second electrode 110. It is preferred that the first electrode 108 and the second electrode 110 be formed so that they encircle the circumference of the electrode shell 104. It will be appreciated that a primary function of the electrode shell 104 is to carry the first electrode 108 and the second electrode 110. The electrodes 108 and 110 are fabricated from a conductive material. The preferred conductive material for the electrodes 108 and 110 is, selected from materials available in the industry and in particular embodiments is a resilient or elastic material. A material such as carbon impregnated silicon rubber is one of the presently preferred materials for use in the embodiments of the present invention but other materials can also be used within the scope of the present invention.

One preferred electrical characteristic of the material used for the electrodes 108 and 110 is a resistance of 12 Ω per cm.

Those skilled in the art will readily appreciate the electrical characteristics which are desirable for the electrodes used in connection with the embodiments of the present invention. It will be appreciated that it is also within the scope of the present invention to position one electrode within the body cavity while positioning another electrode outside of the body cavity in some applications.

FIGS. 6A and 6B provide detailed side and front views, respectively, showing the band configuration of the first electrode 108. While many different dimensions can be used within the scope of the present invention, exemplary dimensions for the first electrode are:

| Reference No. | Exemplary Dimension |
| --- | --- |
| 144 | 0.995 inch |
| 146 | 0.785 inch |
| 148 | 0.375 inch |

It is to be understood that other dimensions can be used in accordance with the present invention. When selecting other dimensions, consideration such as the fit and functioning of the probe 100 should be appreciated.

Referring now to FIG. 2, each of the electrodes 108 and 110 are connected to a respective electrical conductor 122 and 124. The electrical conductors 122 and 124 may be coupled to the electrodes 108 and 110 in any suitable manner. It is preferred that the electrical conductors 122 and 124 pass through bores 113 and 115 provided in the electrode shell 104 such that an uninsulated portion of the electrical conductors 122 and 124 is positioned under the respective electrode 108 and 110 and makes electrical contact therewith.

As can be seen best in the cross sectional view of FIG. 2, each of the electrodes 108 and 110 is preferably positioned in a channel which is formed about the circumference of the electrode shell 104. Advantageously, the electrodes 108 and 110 are formed as bands, preferably as represented in FIGS. 6A and 6B. The electrodes 108 and 110 are positioned on the electrode shell 104 after the electrode shell 104 has been formed. The preferred electrodes 108 and 110 are fabricated from a somewhat flexible material which allows positioning of the electrodes 108 and 110 after fabrication of the electrode shell. Positioning the electrodes 108 and 110 after the fabrication of the electrode shell 104 provides much simpler and economical fabrication of the electrode carrier 102 than when the conductive electrodes must be fabricated simultaneously with the insulative structures (which in the prior art are generally fabricated from silicone) which carries the electrodes.

Providing an indication of the pressure which the pelvic floor muscles are exerting is beneficial when carrying out treatments. Thus, a pressure sensor 126 is provided on the interior of the electrode shell 104. The pressure sensor 126 generates a signal which is proportional to the pressure being exerted upon the electrode carrier 102. In the preferred application of the present invention, the pressure sensor 126 detects the pressure exerted by the vaginal wall.

The pressure is communicated to the pressure sensor 126 via an aperture 117 provided in the electrode shell 104. A flexible band 116 is positioned on the exterior of the electrode shell 104 so it is located between the first electrode 108 and the second electrode 110. As shown best in the cross sectional view of FIG. 2, the flexible band 116 is positioned in a channel formed about the circumference of the electrode shell 104. Preferably, the flexible band 116 is fabricated from a suitable flexible material such as medical grade polyvinyl chloride which is positioned on the electrode shell 104 after the fabrication of the electrode shell 104. A secondary channel 118 is provided to accommodate the flexing of the flexible band 116. In one preferred embodiment, a gelatinous material, as is known in the art, is placed in a portion of, or entirely fills, the secondary channel 118 and the aperture 117 and functions as part of a means for conveying the pressure from the resilient band 116 to the pressure sensor 126. The pressure exerted upon the flexible band 116 is transmitted through the secondary channel 118, the aperture 117, to the pressure sensor 126.

The pressure sensor 126 preferably includes one of the pressure transducers available in the industry and is most preferably a pressure transducer which includes a silicon diaphragm upon which is patterned a resistive Whetstone bridge circuit which causes a change in current flow through the circuit when the pressure exerted upon the diaphragm changes. The electrical signal generated by the pressure sensor 126 is conveyed via conductors shown at 128 in the cross sectional view of FIG. 2.

Also represented in FIG. 2 is a vent orifice provided on the end of the electrode shell 104. A vent tube 120 is connected to the vent orifice 106 with the vent tube 120 leading to a sheath 130. The vent tube 120 leads up the sheath 130 to a location where the vent tube 120 is vented to atmospheric pressure through a plug 114. Thus, the signals generated by the pressure sensor 126 are more accurate than if the vent orifice 106 were not vented to atmosphere. Inclusion of the vent orifice 106 and vent tube 120 ensures that the pressure sensor 126 will respond to the pressure exerted by the body cavity, for example the pressure exerted by the pelvic floor muscles, rather than being influenced by fluids which may be present in the body cavity. The sheath 130 contains the vent tube 120, electrical conductors 122 and 124, and conductors 128 and is preferably terminated with the plug 114 all of which can be selected from those available in the industry. The electrical components should be selected from those which will provide the necessary secure electrical connections.

In accordance with the present invention, a signal generator/monitor 134 is provided. The signal generator/monitor 134 includes a receptacle 142 which is selected to mate with the plug 114 and provide the required electrical connections. The signal generator/monitor 134 provides the electrical signal(s) which are conveyed to the first electrode 108 and the second electrode 110 which provide transcutaneous muscle stimulation. The signal generator/monitor 134 provides a user input device 138 which allows a user to input desired instructions to the signal generator/monitor 134. The signal generator/monitor 134 also includes a power supply 136, which can include a battery, for powering the signal generator/monitor 134. Also included is a stimulation signal generator 150.

A user display 140 is also preferably provided. The user display 140 preferably provides a humanly perceptible display of the pressure detected by the pressure sensor 126. When treating urinary incontinence in females, providing feedback to the user on the intravaginal pressure being caused by the electrical stimulation is very useful in adjusting the electrical stimulation which is applied by the first electrode 108 and the second electrode 110 for greatest benefit. Moreover, the system represented in FIG. 2 can be used to determine the intravaginal pressure being exerted by the user when electrical stimulation is not being administered so that the user can gauge the increase in the strength of the pelvic floor muscles. The user display 140 can preferably provide a real time indication of the stimulation being provided and/or the pressure being detected by the pressure sensor 126.

To assist the with the insertion of the electrode carrier 102, a handle 112 is attached to the electrode shell 104. The handle 112 is also preferably fabricated from polyvinyl chloride using injection molding techniques. The electrode carrier 102 can be used with the handle 112, used separately from the handle 112, or the handle 112 may be removable from the electrode carrier 102 after placement of the electrode carrier 102. It is preferred that the interior of the handle 112 be hollow as shown best in FIG. 2 and that the sheath 130 exit through an opening provided in the end of the handle 112.

A plug 114 is preferably molded onto the end of the sheath 130. The electrical conductors 122, 124, and 128 are mated to connections internal to the plug 114 so that proper electrical connections can be made to the signal generator/monitor 134 via a receptacle represented schematically at 142.

Figure 3:
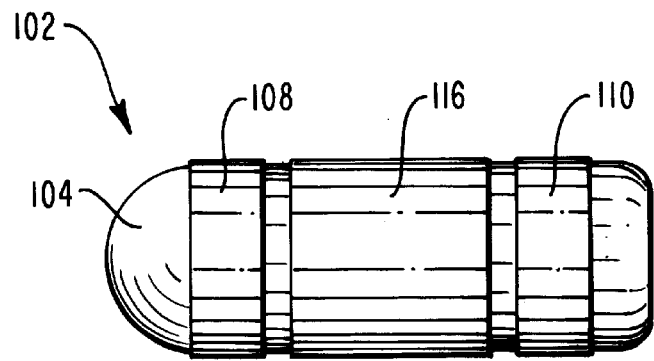
FIG. 3 is a detailed view of the electrode carrier represented in FIG. 1.

FIG. 3 provides a side view of the electrode shell 104 with the first electrode 108 and the second electrode 110 and the flexible band 116 in position on the electrode shell 104. It will be appreciated that the relative position of the first electrode 108 and the second electrode 110 and the flexible band 116 can be altered from the preferred positions represented in the figures. Moreover, it is also within the scope of the present invention to change the shape, width, height, or configuration of such structures.

Figure 4:
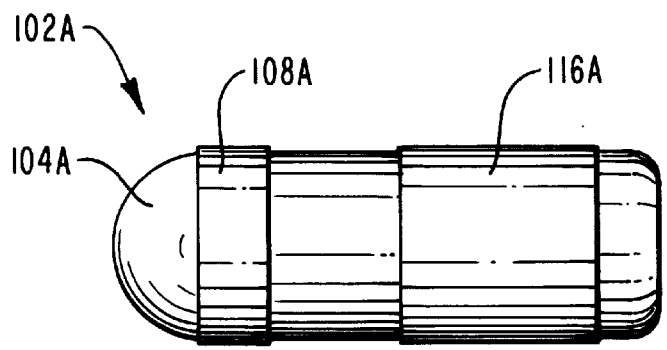
FIG. 4 is a detailed view of an alternative electrode carrier in accordance with the present invention.

FIG. 4 is a detailed view of an alternative electrode carrier, generally designated 102A, which may be used in a manner as described in the application of electrode carrier 102. The alternative electrode carrier 102A includes a first electrode 108A, which is positioned on an alternative electrode shell 104A in a manner similar to that explained in connection with electrode 108 in FIG. 2. Also represented in FIG. 4 is a second electrode/flexible band 116A. The second electrode/flexible band 116A functions both to convey electrical current to the body and facilitate pressure sensing. It will be appreciated that both electrical connections and pressure sensing functions can be carried out with structures similar to those described in connection with the second electrode 110 and the flexible band 116 described in connection with FIG. 2. Significantly, a conductive material such as the preferred material for fabrication of first electrode 108, can be made flexible enough for use as a second electrode/flexible band 116A. It will be understood that combining the functions of carrying electrical current and transmitting pressure allows the embodiment represented in FIG. 4 to be fabricated even more economically.

Figure 5:
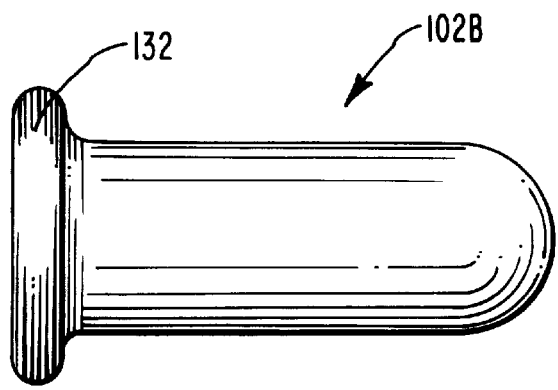
FIG. 5 is a detailed view of an electrode insertion device in accordance with the present invention.

FIG. 5 is a detailed view of another electrode carrier 102B in accordance with the present invention. The electrode carrier 102B illustrated in FIG. 5 can preferably include all of the structures described in connection with FIGS. 1–4 (but not represented in FIG. 5) and additionally includes a depth restriction flange 132. The depth restriction flange 132 is provided to assist with the insertion of the electrode carrier 102B the proper depth in the body cavity, for example, a vagina. It will be appreciated that it is within the scope of the present invention to provide a mechanism for altering the location of the depth restriction flange 132 so that once a user determines the optimum placement of the electrode carrier 102B the depth restriction flange will assist in finding the optimum placement in the future. It is to be understood that a series of electrode carriers 102B can be fabricated in different sizes and with the depth restriction flange 132 in a different position on the different electrode carriers 102B.

FIG. 7 is a cross sectional view of another embodiment of the present invention which is particularly economical to fabricate. FIG. 7 provides a cross sectional view of the additional probe assembly generally represented at 200 in FIG. 7. Similarly to the embodiment represented in FIGS. 1 and 2, the probe 200 includes, as seen best in the cross sectional view of FIG. 7, a hollow electrode shell 202 and a handle 212 is provided.

Provided on the exterior of the electrode shell 202 are a first electrode 204 and a second electrode 206. It is preferred that the first electrode 204 and the second electrode 206 be formed so that they encircle the circumference of the electrode shell 204.

As shown in FIG. 7, each of the electrodes 204 and 206 are connected to a respective electrical conductor 208 and 210. The electrical conductors 208 and 210 pass through a sheath 214 and make appropriate electrical connections at plug 216.

Figure 8:
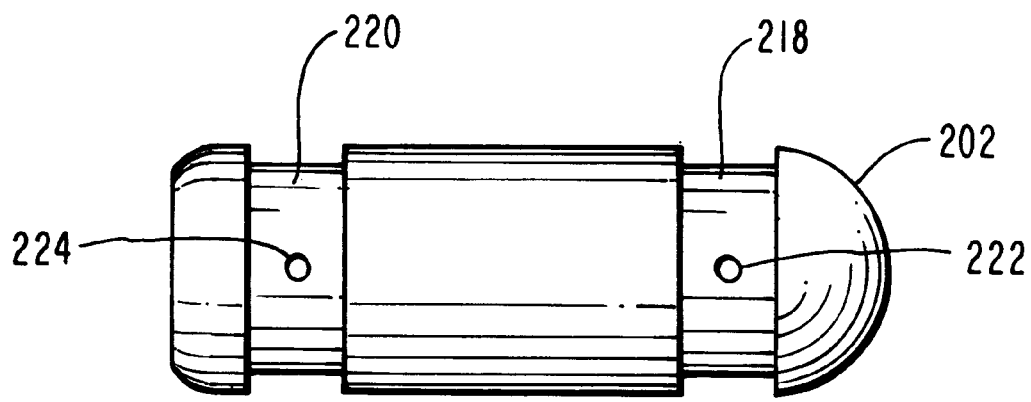
FIG. 8 is a detailed side view of the electrode carrier represented in FIG. 7.

FIG. 8 is a detailed side view of the electrode shell 202 represented in FIG. 7 in which the electrodes 204 and 206 have not yet been positioned. As seen in the side view of FIG. 8, a first channel 218 and a second channel 220 are formed about the circumference of the electrode carrier 202. Bores 222 and 224 are provided in the electrode shell 202 such that the electrical conductors 208 and 210 can pass through the electrode shell 202 and make electrical contact with electrodes 204 and 206 in a manner similar to that explained in connection with electrodes 108 and 110 (see FIG. 2).

Electrodes 202 and 204 can be fabricated from many different materials. In particular, the electrodes may be fabricated from materials which provide an economical probe 200. In some cases, the probe 200 can be economically fabricated so that it can be disposed of after a single use or after just a few uses. The economical fabrication of the probe particularly facilitates the utilization of the probe by a user without immediate supervision of a medical professional.

The electrodes 202 and 204 can be fabricated from a resilient and/or elastic material or from other conductive materials. For example, the electrodes 202 and 204 can be fabricated from solid bands of metal, from conductive foil which is placed on the electrode shell 202, or from selectively deposited conductors. Such selectively deposited conductors can preferably include silver, silver chloride, aluminum, chromium, and nickel. Those skilled in the industry will appreciate the modifications which will be made to the electrode shell 202 (and to electrode shell 104 and electrode shell 104A shown in FIGS. 2 and 4, respectively) in order to accommodate these different materials from which the electrodes can be fabricated.

From the forgoing, it will be appreciated that the present invention provides a system for treating female urinary incontinence which can be used by a patient without the immediate supervision of a medical practitioner. The present invention also provides a device for providing electrical stimulation to a body cavity which is inexpensive and which can be economically manufactured.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A device for applying electrical stimulation to a body cavity and measuring the pressure exerted by the body cavity, the device comprising:

first conductive means for conveying an electrical current to the body cavity;

second conductive means for conveying an electrical current to the body cavity;

pressure sensing means for sensing pressure exerted by the body cavity;

means for supporting at least a portion of the first conductive means and at least a portion of the second conductive means in a spaced apart relationship within the body cavity and for holding at least a portion of the pressure sensing means within the body cavity such that the pressure exerted by the body cavity can be expressed as an electrical signal, the means for supporting comprises an electrode carrier fabricated from an injection molded thermoplastic material having a rigid and hard outer surface, the outer surface in direct contact with the body cavity when the means for supporting is inserted into the body cavity;

means for conveying to a human the pressure expressed as the electrical signal in a humanly perceptible manner; and means for generating a stimulation current and conveying the stimulation current to the first and second conductive means.

2. A device as defined in claim 1 wherein the first conductive means comprises an electrode fabricated from a material selected from the group consisting of: carbon impregnated silicon rubber; silver; silver chloride; aluminum; chromium; and nickel.

3. A device as defined in claim 1 wherein the first conductive means comprises an electrode formed into a band shape.

4. A device as defined in claim 1 wherein the means for supporting comprises a hollow body and wherein the first conductive means and the second conductive means each comprise a band of conductive material encircling the means for supporting.

5. A device as defined in claim 1 wherein the pressure sensing means comprises:

pressure transducer means for outputting an electrical pressure signal proportional to the pressure exerted thereon, the pressure transducer means being disposed in the body cavity when the means for supporting is inserted into the body cavity;

means for conveying the electrical pressure signal to a location outside of the body cavity; and means for electrically isolating the pressure transducer means from the body cavity and for communicating the pressure from the body cavity to the pressure transducer means.

6. A device as defined in claim 5, wherein the pressure transducer means comprises a semiconductor diaphragm which is contained within the means for supporting.

7. A device as defined in claim 5, wherein the means for is conveying the electrical pressure signal comprises:

a first electrical conductor;

a second electrical conductor;

and a plug.

8. A device as defined in claim 5, wherein the means for electrically isolating the pressure transducer means from the body cavity and for communicating the pressure from the body cavity to the pressure transducer means comprises:

a channel in which the pressure transducer means is disposed;

a flexible band placed over the channel and the pressure transducer means such that as the body cavity exerts pressure on the flexible band the flexible band flexes in response thereto; and a gelatinous medium disposed between the flexible band and the pressure transducer means such that the pressure created by the flexing of the flexible band is transmitted to the pressure transducer means.

9. A device as defined in claim 1 further comprising means for venting fluid from within the body cavity to a location outside the body cavity.

10. A device as defined in claim 9, wherein the means for venting comprises:

a vent orifice provided on one end of the means for supporting; and a vent tube connecting the vent orifice to a location outside of the body cavity.

11. A device as defined in claim 1 further comprising a handle extending from the means for supporting.

12. A device as defined in claim 1 wherein the means for conveying to a human comprises a visual display.

13. A device as defined in claim 1 wherein the means for generating a stimulation current comprises a stimulation current generator.

14. A device as defined in claim 1 wherein the second conductive means and the pressure sensing means comprise a single conductive electrode formed into a band shape.

15. A system for treating urinary incontinence in females comprising:

an electrode carrier, the electrode carrier having a generally cylindrical shape for insertion into the female's vagina and comprising a thermoplastic insulative material, the thermoplastic insulative material comprising an injection molded polyvinyl chloride material which is rigid and has a hard outer surface;

a first channel formed about the circumference of the electrode carrier;

a first conductive electrode placed in the first channel;

a second channel formed about the circumference of the electrode carrier, the second channel formed a distance from the first channel;

a second conductive electrode placed in the second channel;

means for generating an electrical signal;

first means for conveying the electrical signal to the first conductive electrode;

second means for conveying the electrical signals to the second conductive electrode a third channel formed about the circumference of the electrode carrier;

a resilient band placed in the third channel, the resilient band flexing in accordance with the pressure exerted thereon by the vagina;

means for generating an electrical pressure signal which is proportional to the pressure exerted upon the resilient band by the vagina;

means for conveying the pressure from the resilient band to the means for generating; and means for conveying the electrical pressure signal in a humanly perceptible manner.

16. A system as defined in claim 15, wherein the first conductive electrode comprises an electrode fabricated from a material selected from the group consisting of: carbon impregnated silicon rubber; silver; silver chloride; aluminum; chromium; and nickel.

17. A system as defined in claim 15, wherein the first conductive electrode comprises an electrode formed into a band shape.

18. A system as defined in claim 15, wherein the electrode carrier comprises a hollow body and wherein the first conductive electrode and the second conductive electrode each comprise a band of conductive material encircling the hollow body.

19. A system as defined in claim 15, wherein the means for generating a pressure signal comprises:

pressure transducer means for outputting an electrical pressure signal proportional to the pressure exerted thereon, the pressure transducer means being disposed in the body cavity when the means for supporting is inserted into the body cavity; and means for conveying the electrical pressure signal to a location outside of the body cavity.

20. A system as defined in claim 15, wherein the means for generating an electrical pressure signal comprises a semiconductor diaphragm which is contained within the means for supporting.

21. A system as defined in claim 15, wherein the means for displaying the electrical pressure signal comprises:

a first electrical conductor;

a second electrical conductor;

and a plug.

22. A system as defined in claim 15, further comprising a gelatinous medium disposed in the third channel between the flexible band and the means for generating an electrical pressure signal such that the pressure created by the flexing of the flexible band is transmitted thereto.

23. A system as defined in claim 15, further comprising means for venting fluid from within the body cavity to a location outside the body cavity.

24. A system as defined in claim 23, wherein the means for venting comprises:

a vent orifice provided on one end of the electrode carrier; and a vent tube connecting the vent orifice to a location outside of the body cavity.

25. A system as defined in claim 15, further comprising a handle extending from the electrode carrier.

26. A system as defined in claim 15, wherein the means for conveying the electrical pressure signal comprises a visual display.

27. A system for applying electrical stimulation to a body cavity, the system comprising:

means for generating an electrical stimulation signal; and a device configured for insertion into and retention in the body cavity, the device consisting essentially of:

first conductive means for conveying an electrical current to the body cavity;

second conductive means for conveying an electrical current to the body cavity, the second conductive means being spaced from the first conductive means and being electrically insulated therefrom;

means for supporting the first conductive means and the second conductive means such that the first and second conductive means can be inserted into and retained in the body cavity, the means for supporting comprising a hollow shell which is hard and rigid and is fabricated from an injection molded thermoplastic material, the thermoplastic material comprising a polyvinyl chloride material, the polyvinyl chloride having a hardness greater than medical grade silicone and the polyvinyl chloride material being in direct contact with the body cavity when inserted therein; and means for conveying the electrical stimulation signal from a location outside of the body cavity to the first conductive means and the second conductive means such that electrical stimulation is applied to the body cavity.

28. A device as defined in claim 27, wherein the first conductive means comprises an electrode fabricated from a material selected from the group consisting of: carbon impregnated silicon rubber; silver; silver chloride; aluminum; chromium; and nickel and combinations thereof.

29. A device as defined in claim 27, wherein the first conductive means comprises an electrode formed into a band shape.

30. A device as defined in claim 27, wherein the first conductive means comprises a band of conductive material encircling the means for supporting.

31. A device as defined in claim 27, wherein the means for generating an electrical stimulation signal comprises:

a first electrical conductor;

a second electrical conductor; and a plug.

* * * * *